US012564197B2

(12) United States Patent
Colson et al.

(10) Patent No.: US 12,564,197 B2
(45) Date of Patent: Mar. 3, 2026

(54) LACTIC ACID BACTERIA COMPOSITION FOR PREPARING FERMENTED FOOD PRODUCTS

(71) Applicants:Chr. Hansen A/S, Hoersholm (DK); Compagnie Gervais Danone, Paris (FR)

(72) Inventors: Benoit Colson, Arpajon (FR); Sonja Bloch, Hoersholm (DK); Gaelle Lettier Buchhorn, Hoersholm (DK); Nanna Christensen, Hoersholm (DK); Marie-Agnès Soucé, Paris (FR); Laurent Marchal, Paris (FR); Anne Depierris, Paris (FR); Fanny Larrere, Paris (FR)

(73) Assignees: Chr. Hansen A/S, Hoersholm (DK); Compagnie Gervais Danone, Paris (FR)

( * ) Notice: Subject to any disclaimer, the term of this patent is extended or adjusted under 35 U.S.C. 154(b) by 451 days.

(21) Appl. No.: 17/927,131

(22) PCT Filed: May 31, 2021

(86) PCT No.: PCT/EP2021/064542
§ 371 (c)(1),
(2) Date: Nov. 22, 2022

(87) PCT Pub. No.: WO2021/240015
PCT Pub. Date: Dec. 2, 2021

(65) Prior Publication Data
US 2023/0200406 A1 Jun. 29, 2023

(30) Foreign Application Priority Data
May 29, 2020 (EP) .................................... 20177299

(51) Int. Cl.
| | |
|---|---|
| *A23C 9/123* | (2006.01) |
| *C12N 1/20* | (2006.01) |
| *C12N 1/205* | (2026.01) |
| *C12N 9/12* | (2006.01) |
| *C12N 15/10* | (2006.01) |
| *C05B 17/00* | (2006.01) |
| *C05B 17/02* | (2006.01) |
| *C12R 1/225* | (2006.01) |
| *C12R 1/46* | (2006.01) |

(52) U.S. Cl.
CPC ............ *A23C 9/1238* (2013.01); *C12N 1/205* (2021.05); *C12N 9/1205* (2013.01); *C12N 15/1034* (2013.01); *C12R 2001/225* (2021.05); *C12R 2001/46* (2021.05); *C12Y 207/01002* (2013.01)

(58) Field of Classification Search
CPC .... A23C 9/1238; C12N 1/205; C12N 9/1205; C12N 15/1034; C12R 2001/225; C12R 2001/46; C12Y 207/01002; A23V 2400/11; A23V 2400/123; A23V 2400/137; A23V 2400/21; A23V 2400/249
See application file for complete search history.

(56) References Cited

U.S. PATENT DOCUMENTS

| | | | |
|---|---|---|---|
| 6,875,601 | B1 | 4/2005 | Benbadis et al. |
| 10,813,367 | B2 | 10/2020 | Garrigues et al. |
| 2021/0274800 | A1 | 9/2021 | Bloch et al. |

FOREIGN PATENT DOCUMENTS

| | | | | |
|---|---|---|---|---|
| WO | WO-2011092300 A1 | * | 8/2011 | ............... A23C 9/12 |
| WO | WO-2015/193459 A1 | | 12/2015 | |
| WO | WO-2018/177835 A1 | | 10/2018 | |
| WO | WO-2019/197051 A1 | | 10/2019 | |

OTHER PUBLICATIONS

Sørensen et al. Applied and environmental microbiology 82.12 (2016): 3683-3692. (Year: 2016).*
Sorensen et al. Applied and environmental microbiology 82.12 (2016): 3683-3692. (Year: 2016).*

* cited by examiner

*Primary Examiner* — Erik Kashnikow
*Assistant Examiner* — Janice Y Silverman
(74) *Attorney, Agent, or Firm* — Yoshimi D. Barron

(57) ABSTRACT

The invention relates to a composition for producing a fermented milk product comprising: (i) a starter culture comprising a glucose-fermenting *Streptococcus thermophilus* (St) strain and a glucose-fermenting *Lactobacillus delbrueckii* subsp. *bulgaricus* (Lb) strain; and (ii) a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene.

13 Claims, No Drawings
Specification includes a Sequence Listing.

SEQUENCE LISTING

<160> NUMBER OF SEQ ID NOS: 6

<210> SEQ ID NO 1
<211> LENGTH: 966
<212> TYPE: DNA
<213> ORGANISM: Streptococcus thermophilus

<400> SEQUENCE: 1

-continued

```
atgagtaaga aactcttagg tattgacctt ggtggaacaa ctgttaagtt tggtattttg      60
actgcagatg gtgaagttca agaaaaatgg gctattgaaa caaatacgtt tgaaaatggt     120
agccacattg ttcctgacat tgtagaatct ttgaaacacc gtttggaatt gtatggactt     180
actgctgaag attttattgg aattggtatg ggatctccag gtgcagttga ccgagaaaat     240
aaaacagtaa cgggtgcctt taacttgaac tgggcagaaa ctcaagaagt tggctctgtt     300
attgaaaaag aacttggtat tccattcgct attgataatg atgctaatgt ggctgcactg     360
ggtgaacgtt gggttggtgc tggtgctaac aatcggaatg ttgtctttat aacattgggt     420
acaggtgttg gtggcggtgt tatcgctgat ggtaacttaa ttcatggtgt tgccggtgct     480
ggtggggaaa ttggtcacat tattgttgaa cctgacacag atttgagtg tacttgcgga      540 aacaaggggt gtctggaaac tgtagcttca gcaacaggta ttgtacgtgt agcacatcat     600
ttggcagaaa atacgaagg aaactcttct attaaagctg ctgtagacaa tggtgagttt     660
gtgacaagta agatattat cgtagctgct actgaaggtg ataagtttgc tgacagcatt      720
gttgataaag tctctaaata cctcagactt gcaacagcaa acatctcaaa cattcttaac     780
ccagattctg tcgttatcgg tggtggtgtt tctgccgcag agaattctt gcgtagtcgt       840 gttgaaggat actttacacg ttatgcattc ccacaagttc gccgtacaac aaaagtgaaa     900
ttagcggagc ttggaaatga tgcaggaatc attggagctg ctagtcttgc ttatagtatt     960
gacaaa                                                                966
```

```
<210> SEQ ID NO 2
<211> LENGTH: 322
<212> TYPE: PRT
<213> ORGANISM: Streptococcus thermophilus

<400> SEQUENCE: 2

Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
```

-continued

```
              195                 200                 205
Ser Ser Ile Lys Ala Ala Val Asp Asn Gly Glu Phe Val Thr Ser Lys
        210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Arg Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
            275                 280                 285

Ala Phe Pro Gln Val Arg Arg Thr Thr Lys Val Lys Leu Ala Glu Leu
        290                 295                 300

Gly Asn Asp Ala Gly Ile Ile Gly Ala Ala Ser Leu Ala Tyr Ser Ile
305                 310                 315                 320

Asp Lys

<210> SEQ ID NO 3
<211> LENGTH: 909
<212> TYPE: DNA
<213> ORGANISM: Streptococcus thermophilus

<400> SEQUENCE: 3
atggctgaaa aaattcaatt atctcaagcg gatcgtaaaa aggtttggtg gcgctcacaa        60
ttcttgcaag gtgcatggaa ctatgaacgt atgcaaaact tgggttgggc ttactcactc       120
attcctgcta tcaaaaaact ttatactaac aaagaggacc aagccgcagc tcttaaacgt       180
cacttggaat cttcaacac tcacccttac gtagctgctc ctatcatagg ggttccctta       240
gctcttgaag aagaaaaagc taatggtact gaaatcgaag atgcggctat ccaagggtt       300 aaaatcggta tgatgggtcc acttgccggt atcggtgacc ctgtcttctg gttcacaatt       360
cgtccaattc ttggtgccct tggtgcatca ttggcacaag ctggtaacat tgctggtcca       420
cttatcttct tcattggttg gaaccttatc cgcatggcct tcttgtggta cactcaagaa       480
cttggttaca agcaggttc agaaatcact aaagacatat ctggtggtat cttgaaagat       540
attactaaag gggcatcaat acttggtatg ttcatcttgg ccgtcctcgt tgaacgttgg       600
gtatctgtcg tcttcactgt aaagcttcca ggtaaagttt tgcctaaagg tgcttatatt       660
gaatggccaa aggatatgt tactggtgac caactaaaaa ctatccttgg tcaagtcaac       720
gataagctta gctttgataa gattcaagtc gataccctac aaaaacaatt ggattcatta       780
attccaggtt tgacgggact ctcccttact tttgcatgta tgtggttgct taagaagaaa       840
gtttcaccaa tcacaatcat catcggactc tttgtagttg gtattattgc aagcttcttc       900
ggaatcatg                                                               909

<210> SEQ ID NO 4
<211> LENGTH: 303
<212> TYPE: PRT
<213> ORGANISM: Streptococcus thermophilus

<400> SEQUENCE: 4

Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30
```

-continued

```
Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Ile Gly Val Pro Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110

Asp Pro Val Phe Trp Phe Thr Ile Arg Pro Ile Leu Gly Ala Leu Gly
            115                 120                 125

Ala Ser Leu Ala Gln Ala Gly Asn Ile Ala Gly Pro Leu Ile Phe Phe
        130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Ile Ser Gly Gly
            165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
            245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Ile Ala Ser Phe Phe Gly Ile Met
    290                 295                 300
```

```
<210> SEQ ID NO 5
<211> LENGTH: 828
<212> TYPE: DNA
<213> ORGANISM: Streptococcus thermophilus

<400> SEQUENCE: 5
atgtcagata tgtcaattat ttctgcgatt ttggtcgtag ctgttgcctt ccttgctggt      60
cttgaaagta tccttgacca attccaattc caccaaccac ttgttgcatg taccctcatc     120
ggtgctgcca caggtaacct cactgcaggt atcatgcttg gtggttctct tcaaatgatt     180
acccttgctt gggcaaacat cggtgctgcc gtagctcctg acgttgccct tgcatctgtt     240
gccgctgcca tcattttggt taaaggtggt aaatttacag ctgaaggtat cggtgttgcg     300
attgcaatag ctatcctgct tgcagttgca ggtctcttcc taactatgcc tgttcgtaca     360
gcatctattg cctttgttca tgctgcagat aaagctgcag aacacggaaa catcgctggt     420
gttgaacgtg catactacct cgctctcctt cttcaaggtt tgcgtattgc tgtgccagca     480
gcccttcttc ttgccatccc ggcccaatct gttcaacatg cccttggctt gatgcctgac     540
tggctcaccc atggtttggt tgtcggtggt ggtatggtcg tagccgttgg ttacgccatg     600
```

-continued

```
attatcaata tgatggctac tcgtgaagtt tggccattct tcgccattgg ttttgctttg     660
gcagcaatta gccaattgac acttatcgct cttagtacca ttggtgttgc catcgccttc     720
atctacctca acctttctaa acaaggtggc ggaaatggtg gcggaaatgg tggcggaact     780
tcatctggtt caggcgaccc aatcggcgat atcttggaag actactag                  828
```

```
<210> SEQ ID NO 6
<211> LENGTH: 275
<212> TYPE: PRT
<213> ORGANISM: Streptococcus thermophilus

<400> SEQUENCE: 6

Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
                20                  25                  30

Pro Leu Val Ala Cys Thr Leu Ile Gly Ala Ala Thr Gly Asn Leu Thr
            35                  40                  45

Ala Gly Ile Met Leu Gly Gly Ser Leu Gln Met Ile Thr Leu Ala Trp
        50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
            115                 120                 125

Ala Asp Lys Ala Ala Glu His Gly Asn Ile Ala Gly Val Glu Arg Ala
        130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
                180                 185                 190

Val Val Ala Val Gly Tyr Ala Met Ile Ile Asn Met Met Ala Thr Arg
            195                 200                 205

Glu Val Trp Pro Phe Phe Ala Ile Gly Phe Ala Leu Ala Ala Ile Ser
        210                 215                 220

Gln Leu Thr Leu Ile Ala Leu Ser Thr Ile Gly Val Ala Ile Ala Phe
225                 230                 235                 240

Ile Tyr Leu Asn Leu Ser Lys Gln Gly Gly Gly Asn Gly Gly Gly Asn
                245                 250                 255

Gly Gly Gly Thr Ser Ser Gly Ser Gly Asp Pro Ile Gly Asp Ile Leu
                260                 265                 270

Glu Asp Tyr
        275
```

LACTIC ACID BACTERIA COMPOSITION FOR PREPARING FERMENTED FOOD PRODUCTS

CROSS-REFERENCE TO RELATED APPLICATIONS

The present application is the U.S. National Stage of International Application No. PCT/EP2021/064542, filed May 31, 2021, and claims priority to European Patent Application No. 20177299.3, filed May 29, 2020.

FIELD OF INVENTION

The present invention relates to composition and methods for producing a fermented milk product such as e.g. yoghurt. In particular the invention relates to composition and methods for reducing post-acidification.

BACKGROUND OF THE INVENTION

Most of the current methods for producing fermented milk products can be characterized by the following steps:
(a) a milk substrate is fermented by the addition of a starter culture comprising lactic acid bacteria (LAB) capable of metabolizing glucose obtained from lactose present in the milk;
(b) during fermentation the LAB metabolizes glucose and produces lactic acid (acidification), which causes a decrease of the pH from an initial range of 6.4 to 6.8 (for cow milk) to a range between pH 3.8 and 4.7;
(c) once the fermented product at issue has reached a desired pH, fermentation is terminated by rapid cooling of the fermented milk product.

This method is for example used to produce yoghurt and yoghurt beverages.

Without cooling of the milk product to terminate fermentation the process would continue and cause further acidification of the product after the target pH has been reached i.e. post-acidification.

One disadvantage of rapid cooling is that it leads to loss of texture in the product. Omitting the step of rapid cooling is therefore desirable and would furthermore spare a unit operation and thus reduce production costs.

Despite presence of a rapid cooling step in methods for producing fermented milk products post-acidification is still observed i.e. production of lactic acid by the LAB after the termination of fermentation at the desired pH. Post-acidification is considered to represent one of the most important problems during methods for producing fermented milk products. The further decrease of the pH value during storage (incl. processing, packaging, transport, and storage) of the fermented milk product leads to problems with elevated acidity and reduced shelf life.

Post-acidification therefore also has a negative impact on the shelf life of yoghurt. The shelf life of a yoghurt varies from 30 to 50 days depending on the country. During this time post-acidification changes the quality of the yoghurt causing a sour product (flavor change) and high whey separation (texture change). Usually the quality of yoghurt is maintained as much as possible by keeping the product at a temperature between 4° C. and 8° C. during storage. At this temperature bacteria will only have a low activity. However, in many countries it is difficult to maintain the cool-chain during storage.

As a consequence, the manufacture of Extended Shelf Life Yoghurt (ESL yoghurt), is of high interest, in particular in countries where it is difficult to maintain the cool-chain. The prior art methods of producing ESL yoghurt include a heat treatment step (typically 65° C. for 30 sec) after the fermentation. The treatment causes a significant decrease in the number of bacteria used for fermentation as well as in the number of yeasts and molds. The heating step also inhibits the activity of enzymes present in the yoghurt. As a consequence, the product may obtain an extended shelf life of up to 9 months, wherein no or only low post-acidification and post-flavor changes are observed.

However, the heat treatment has a negative effect on the quality of the yoghurt and changes in flavor and texture are obtained. A further negative effect of the heat treatment is that the health benefits obtained by the presence of live bacteria such as probiotics are diminished or lost.

One of the approaches for controlling post-acidification resides in producing milk products with a relatively acidic pH. In these methods the further growth of the LAB and the production of lactic acid is inhibited by the acidic pH. However, the further production of lactic acid is only inhibited and not completely terminated and the method is obviously unsuitable for the production of fermented milk products with a mild taste.

It was assumed that post-acidification is controlled by the metabolic activity of *L. bulgaricus* and caused by peptide uptake and strains with a deficiency in amino acid metabolism were generated to control post-acidification (US2010/0021586 and WO2006/042862A1). Other approaches for controlling post-acidification have been described in the prior art and include processes based on the use of specific LAB strains characterized by weakly post-acidifying activity (WO2010/139765).

An alternative approach for minimizing post-acidification is based on the control of the ratio of protein to lactose, the control of the buffering capacity and the maintenance of the buffering capacity and the pH within a predetermined range during fermentation (WO2013/169205). However, this approach requires the determination of a number of process parameters during fermentation and may require the addition of proteins or lactose or a buffer to the fermentation medium to ensure that the predetermined ranges are maintained during fermentation.

WO2013/160413 discloses *Streptococcus thermophilus* strains and *Lactobacillus delbrueckii* subsp. *bulgaricus* strains with enhanced properties for natural sweetening of food products and for decreasing the lactose content of fermented milk, and method of screening and isolating such strains.

WO2015/193459 discloses a method of producing a fermented milk product with a reduced level of post-acidification obtained by depletion of the lactose contained in the milk base during fermentation resulting in no or very little growth of the starter culture during subsequent storage. One embodiment uses a mixture of four lactic acid bacteria strains with a deficiency in glucose metabolism, and another embodiment uses a mixture of lactose-deficient lactic acid bacteria strains.

The object of the present invention is to provide a composition for producing a fermented milk product with reduced post-acidification.

SUMMARY OF INVENTION

This object is achieved with the present invention, which is directed to a composition for producing a fermented milk product comprising:

(i) a starter culture comprising a glucose-fermenting *Streptococcus thermophilus* (St) strain and a glucose-fermenting *Lactobacillus delbrueckii* subsp. *bulgaricus* (Lb) strain; and (ii) a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene.

It is well known that for conventional starter cultures for producing fermented milk products comprising a conventional *Streptococcus thermophilus* strain and a conventional *Lactobacillus delbrueckii* subsp. *bulgaricus* strain, there is a risk of post-acidification during storage, i.e. from the end of the lactic acid bacterium fermentation of the milk until the time of consumption, even at refrigerated temperatures. Such post-acidification is caused by the continued growth of the lactic acid bacteria during storage leading to further acidification of the fermented milk product as well as the formation of off-flavors, such as free amino acids, e.g. glutamic acid.

It has surprisingly been found that the post-acidification by a conventional starter culture in a fermented milk product may be reduced significantly by adding to a conventional starter culture a glucose-deficient *Streptococcus thermophilus* strain. This is a very surprising finding, since the glucose-deficient *Streptococcus thermophilus* strain has been developed with a completely different object in mind, viz. to increase the level of natural sweetness in a fermented milk product, whereas any effect on post-acidification has previously not been recognized and is unexpected. Moreover, the glucose-deficient *Streptococcus thermophilus* strain not only does not itself cause post-acidification but apparently also reduces the post-acidification of the strains of the conventional starter culture, which effect is previously unrecognized and unpredictable. In particular, the mechanism behind the reduction of the post-acidification of the strains of the conventional starter culture is not apparent and not obvious.

An additional advantage of the present invention is that the glucose-negative *Streptococcus thermophilus* strain will convert part of the lactose of the milk base to glucose to provide the fermented milk product with a natural sweetness hence reducing the need for adding sugar to the product and to lower the lactose content of the milk base for the benefit of consumers intolerant to lactose.

In a second aspect the invention relates to a method for producing a fermented milk product comprising inoculating and fermenting a milk substrate with the composition of the invention.

In a third aspect the invention relates to a fermented milk product obtained by the method of the invention.

In a fourth aspect the invention relates to use of the composition according to the invention for the preparation of a fermented milk product.

DETAILED DISCLOSURE OF THE INVENTION

Definitions

As used herein, the term "lactic acid bacterium" abbreviated "LAB" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In connection with the present invention, the expression "increasing the sweetness" means an increase in sweetness as compared to the sweetness produced by a mother strain not carrying a mutation in the DNA sequence of the glcK gene encoding a glucokinase protein, wherein the mutation inactivates the glucokinase protein or has a negative effect on expression of the gene.

The expression "CFU" means Colony Forming Units.

In connection with the present invention, the expression "conventional" in relation to a lactic acid bacterium strain means a glucose-fermenting strain.

Glucose-Deficient *Streptococcus thermophilus* Strain of the Composition of the Invention In some countries, the legal definition of yoghurt requires the presence of strains of both *Streptococcus thermophilus* and *Lactobacillus delbrueckii* subsp. *bulgaricus*. Both species generate desirable amounts of acetaldehyde, an important flavor component in yoghurt.

In order to meet the requirements of the food industry, it has become desirable to develop new strains, in particular *Streptococcus thermophilus* strains and *Lactobacillus delbrueckii* subsp. *bulgaricus* strains, which produce more natural sweetness directly in the fermented product (inner sweetness) without contributing extra calories.

*Streptococcus thermophilus* is one of the most widely used lactic acid bacteria for commercial milk fermentation where the organism is normally used as part of a mixed starter culture, the other component being a *Lactobacillus* sp., e.g. *Lactobacillus delbrueckii* subsp. *bulgaricus* for yoghurt.

Only the glucose portion of the lactose molecule is fermented by *Streptococcus thermophilus* and galactose accumulates in fermented milk products when *Streptococcus*

*thermophilus* is used. In yoghurt, wherein high acid concentrations limit the fermentation, free galactose remains.

In order to ensure *Streptococcus thermophilus* strains with a growth performance as optimal as possible, galactose-fermenting strains of *Streptococcus thermophilus* have been exposed to the selective agent 2-deoxyglucose. Typically 2-deoxyglucose resistant mutants have mutations in the gene encoding glucokinase (glcK) and in genes coding for glucose transport. The isolated mutant strains DSM 28889 and DSM 32227, which are resistant to 2-deoxyglucose have a mutation in the glucokinase gene. In addition to a mutation in the glucokinase gene, DSM 28889 and DSM 32227 both have a mutation which means that secreted glucose is not transported back into the cells again.

The term "resistant to 2-deoxyglucose" herein is defined by that a particular mutated bacterial strain has the ability to grow to a colony when streaked on a plate of M17 medium containing 20 mM 2-deoxyglucose after incubation at 40° C. for 20 hours. The presence of 2-deoxygluxose in the culture medium will prevent the growth of non-mutated strains while the growth of the mutated strains is not affected or not affected significantly. Non-mutated strains which can be used as sensitive reference strains in the assessment of resistance preferably include the strains DSM 25838 and DSM 22934.

Surprisingly, 2-deoxyglucose resistant mutants alone are still fully capable of acidifying milk although acidification time is delayed. They are therefore as such useful in fermented milk applications and they have preserved the ability of the mother strains to acidify the milk which is characteristic of yoghurt. Additionally, it was found that the mutants excreted a high level of glucose, when a 9.5% B-milk comprising 0.05% sucrose was inoculated with the mutants and fermented at 40° C. for at least 20 hours. At the same time, very low levels of lactose remain in the fermented milk. Therefore, the use of such strains for producing fermented milk products may have an importance for people with lactose intolerance.

Consequently, the final fermented milk has an increased inner sweetness index calculated as described by Godshall (1988. Food Technology 42(11):71-78).

In one aspect of the present invention, the *Streptococcus thermophilus* strain is a galactose-fermenting mutant strain of *Streptococcus thermophilus*, wherein the mutant strain carries a mutation in the DNA sequence of the glcK gene encoding a glucokinase protein, wherein the mutation inactivates the encoded glucokinase protein or has a negative effect on expression of the gene. Methods for measuring the level of glucokinase activity or the level of expression of the glucokinase gene are readily known (Porter et al. (1982) Biochim. Biophys. Acta, 709:178-186) and include enzyme assays with commercially available kits and transcriptomics or quantitative PCR using materials which are readily available.

In a preferred embodiment of the invention, the glucose-deficient *Streptococcus thermophilus* strain of the invention is 2-deoxyglucose resistant. In a preferred embodiment of the invention, the 2-deoxyglucose resistant *Streptococcus thermophilus* strain of the invention is DSM 28889 or DSM 32227.

A bacterial "strain" as used herein refers to a bacterium which remains genetically unchanged when grown or multiplied. A multiplicity of identical bacteria is included.

The term "galactose-fermenting *Streptococcus thermophilus* strains" as used herein refers to *Streptococcus thermophilus* strains which are capable of growth on/in M17 medium+2% galactose. The galactose-fermenting *Strepto-*

*coccus thermophilus* strains are defined herein as *Streptococcus thermophilus* strains which lower the pH of M17 broth containing 2% galactose as sole carbohydrate to 5.5 or lower when inoculated from an overnight culture at 1% and incubated for 24 hours at 37° C.

The term "the mutation inactivates the glucokinase protein" as used herein refers to a mutation which results in an "inactivated glucokinase protein", a glucokinase protein which, if present in a cell, is not able to exert its normal function as well as mutations which prevent the formation of the glucokinase protein or result in degradation of the glucokinase protein.

In particular, an inactivated glucokinase protein is a protein which compared to a functional glucokinase protein is not able to facilitate phosphorylation of glucose to glucose-6-phosphate or facilitates phosphorylation of glucose to glucose-6-phosphate at a significantly reduced rate. The gene encoding such an inactivated glucokinase protein compared to the gene encoding a functional glucokinase protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of phosphorylation of glucose to glucose-6-phosphate) of the glucokinase protein with at least 50%, such as at least 60%, such as at least 70%, such as at least 80%, such as at least 90%.

The glucokinase activity can be determined by the glucokinase enzymatic assays as described by Pool et al. (2006. Metabolic Engineering 8:456-464).

The term "functional glucokinase protein" as used herein refers to a glucokinase protein which, if present in a cell, facilitates phosphorylation of glucose to glucose-6-phosphate. In particular, a functional glucokinase protein may be encoded by a gene comprising an ORF which has a sequence corresponding to position 1-966 in SEQ ID NO. 1 or a sequence which has at least 85% identity, such as at least 90% identity, such as at least 95% identity, such as at least 98% identity, such as at least 99% identity, to the sequence corresponding to position 1-966 of SEQ ID NO. 1.

The percent identity of two sequences can be determined by using mathematical algorithms, such as the algorithm of Karlin and Altschul (1990. Proc. Natl. Acad. Sci. USA 87; 2264), the modified algorithm described in Karlin and Altschul (1993. Proc. Natl. Acad. Sci. USA 90; 5873-5877); the algorithm of Myers and Miller (1988. CABIOS 4; 11-17); the algorithm of Needleman and Wunsch (1970. J. Mol. Biol. 48; 443-453); and algorithm of Pearson and Lipman (1988. Proc. Natl. Acad. Sci. USA 85; 2444-2448). Computer software for the determination of nucleic acid or amino acid sequence identity based on these mathematical algorithms is also available. For example, the comparison of nucleotide sequences can be performed with the BLASTN program, score=100, wordlength=12. The comparison of amino acid sequences can be performed with the BLASTX program, score=50, wordlength=3. For the remaining parameters of the BLAST programs, the default parameters can be used.

In many countries the use of genetically modified organisms (GMOs) for fermented milk products is not accepted. The present invention instead provides for naturally occurring or induced mutant strains which can provide a desirable accumulation of glucose in the fermented milk product.

Thus, in a preferred embodiment of the present invention the mutant strain is a naturally occurring mutant or an induced mutant.

A "mutant bacterium" or a "mutant strain" as used herein refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with chemical mutagens, UV- or gamma radiation etc. In contrast, a "spontaneous mutant" or "naturally occurring mutant" has not been mutagenized by man. Mutant bacteria are herein, non-GMO (non-genetically modified organism), i.e. not modified by recombinant DNA technology.

"Wild type strain" refers to the non-mutated form of a bacterium, as found in nature.

Terms such as "strains with a sweetening property", "strains which can provide a desirable accumulation of glucose in the fermented milk product" and "strains with enhanced properties for natural sweetening of food products" are used interchangeably herein to characterize an advantageous aspect of using the strains of the present invention in fermentation of milk products.

In a preferred embodiment, the mutant strain of *Streptococcus thermophilus* according to the invention increases the amount of glucose in a 9.5% B-milk to at least 5 mg/mL when inoculated in the 9.5% B-milk at a concentration of $10^6$-$10^7$ CFU/ml and grown at 40° C. for at least 20 hours.

In another preferred embodiment, the mutant strain of *Streptococcus thermophilus* according to the invention increases the amount of glucose in a 9.5% B-milk comprising 0.05% sucrose to at least 5 mg/mL when inoculated in the 9.5% B-milk comprising 0.05% sucrose at a concentration of $10^6$-$10^7$ CFU/ml and grown at 40° C. for at least 20 hours.

In the present context, 9.5% B-milk is boiled milk made with reconstituted low fat skim milk powder to a level of dry matter of 9.5% and pasteurized at 99° C. for 30 min. followed by cooling to 40° C.

In more preferred embodiments of the invention the mutant strain leads to an increase in the amount of glucose to at least 6 mg/mL, such as at least 7 mg/mL, such as at least 8 mg/mL, such as at least 9 mg/ml, such as at least 10 mg/ml, such as at least 11 mg/ml, such as at least 12 mg/ml, such as at least 13 mg/ml, such as at least 14 mg/ml, such as at least 15 mg/ml, such as at least 20 mg/ml, such as at least 25 mg/ml.

The mutant *Streptococcus thermophilus* strains of the invention excrete glucose into the milk when a 9.5% B-milk is inoculated with $10^6$-$10^7$ CFU/ml of a *Streptococcus thermophilus* strain according to the invention and fermented with the *Streptococcus thermophilus* strains according to the invention at 40° C. for at least 20 hours. Preferably, such mutant strains alone will excrete at least 5 mg/ml glucose into a B-milk when 9.5% B-milk is inoculated with $10^6$-$10^7$ CFU/ml of a *Streptococcus thermophilus* strain according to the invention and fermented with the *Streptococcus thermophilus* strains at 40° C. for at least 20 hours. The strains are still fully capable of acidifying milk although acidification time to pH 5 is delayed by 2-5 hours. The final fermented milk contains less than 15 mg/ml lactose in the fermented milk. The final fermented milk consequently has a higher inner sweetness index of approximately 2 fold or more. In one embodiment of the invention, the glucose-deficient

*Streptococcus thermophilus* strain may be lactose-positive or lactose-deficient, however preferably said strain is lactose-positive.

In yet another embodiment, the mutant strain according to the invention can be characterized by its growth pattern. This is illustrated by the finding that the growth rate of the mutant strain is higher in M17 medium+2% galactose than in M17 medium+2% glucose. The growth rate is measured as the development in optical density of the exponentially growing culture at 600 nanometers ($OD_{600}$) with time.

In a preferred embodiment the growth rate is at least 5% higher, such as at least 10% higher, such as at least 15% higher, such as at least 20% higher, in M17 medium+2% galactose than in M17 medium+2% glucose.

Mutation in glcK Gene

In one preferred embodiment the mutation results in the replacement of the codon coding for glycine with the codon coding for arginine in position 249 in SEQ ID NO. 2. Preferably the mutation in the glcK gene results in the replacement of a G with a A in position 745 in SEQ ID NO. 1. Strain DSM 28889 has such a mutation.

In a preferred embodiment the mutation results in the replacement of the codon coding for serine with the codon coding for proline in position 72 in SEQ ID NO. 2 (not shown). Preferably the mutation in the glcK gene results in the replacement of a T with a C in position 214 in SEQ ID NO. 1 (not shown).

In another preferred embodiment the mutation results in the replacement of the codon coding for threonine with the codon coding for isoleucine in position 141 in SEQ ID NO. 2 (not shown).

Preferably, the mutation in the glcK gene results in the replacement of a C with a T on position 422 in SEQ ID NO. 1 (not shown).

It should be emphasized that the glcK gene of a *Streptococcus thermophilus* may be inactivated by other types of mutations in other sites of the glcK gene.

The expression "glcK gene encoding a glucokinase" as used herein refers to any DNA sequence encoding a protein having glucokinase activity, including the specific glucokinase encoded by the DNA sequence of SEQ ID NO.: 1. A glucokinase catalyzes the reaction converting glucose to glucose-6-phosphate.

Mutation Reducing Transport of Glucose into the Cell

In a preferred embodiment the glucose-deficient *Streptococcus thermophilus* strain carries a mutation that reduces the transport of glucose into the cell.

The term "a mutation that reduces the transport of glucose into the cell" as used herein refers to a mutation in a gene encoding a protein involved in transport of glucose which results in an accumulation of glucose in the environment of the cell.

The level of glucose in the culture medium of a *Streptococcus thermophilus* strain can readily be measured by methods known to the skilled person also when the culture medium is a milk substrate.

In preferred embodiments the mutation reduces the transport of glucose into the cell with at least 50%, such as at least 60%, such as at least 70%, such as at least 80%, such as at least 90%.

The transport of glucose into the cell can be determined by the glucose uptake assay as described by Cochu et al. (2003. Appl Environ Microbiol 69(9); 5423-5432).

Preferably, the *Streptococcus thermophilus* strain carries a mutation in a gene encoding a component of a glucose transporter, wherein the mutation inactivates the glucose transporter protein or has a negative effect on expression of the gene.

The component may be any component of a glucose transporter protein which is critical for the transport of glucose. It is e.g. contemplated that inactivation of any component of the glucose/mannose PTS in *Streptococcus thermophilus* will result in inactivation of the glucose transporter function.

The term "the mutation inactivates the glucose transporter" as used herein refers to a mutation which results in an "inactivated glucose transporter", a glucose transporter protein which, if present in a cell, is impaired and not able to exert its normal function as well as mutations which prevent the formation of the glucose transporter protein or result in degradation of the glucose transporter protein.

In particular, an inactivated glucose transporter protein is a protein which compared to a functional glucose transporter protein is not able to facilitate transport of glucose over a plasma membrane or facilitates transport of glucose over a plasma membrane at a significantly reduced rate. The gene encoding such an inactivated glucose transporter protein compared to the gene encoding a functional glucose transporter protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of transport of glucose) of the glucose transporter protein by at least 50%, such as at least 60%, such as at least 70%, such as at least 80%, such as at least 90%.

The glucose transporter activity can be determined by the glucose uptake assay as described by Cochu et al. (2003. Appl Environ Microbiol 69(9); 5423-5432).

The term "functional glucose transporter protein" as used herein refers to a glucose transporter protein which, if present in a cell, facilitates transport of glucose over a plasma membrane.

In a preferred embodiment the glucose-deficient *Streptococcus thermophilus* strain of the invention carries a mutation in the DNA sequence of the manN gene encoding the $IID^{Man}$ protein of the glucose/mannose phosphotransferase system, wherein the mutation inactivates the $IID^{Man}$ protein or has a negative effect on expression of the gene. DSM 28889 has a threonine to proline change at position 79 in the manN gene encoding the $IID^{Man}$ protein of the glucose/mannose phosphotransferase system. Preferably the mutation in the ManN gene results in the replacement of an A with a C in position 235 in SEQ ID NO. 3. Thus, in a preferred embodiment the *Streptococcus thermophilus* strain of the invention carries a mutation in the DNA sequence of the manN gene encoding the $IID^{Man}$ protein of the glucose/mannose phosphotransferase system, wherein the mutation results in the replacement of threonine to proline in position 79 of SEQ ID No. 4.

In another preferred embodiment of the invention the *Streptococcus thermophilus* strain of the invention carries a mutation in the DNA sequence of the manM gene encoding the $IIC^{Man}$ protein of the glucose/mannose phosphotransferase system, wherein the mutation inactivates the $IIC^{Man}$ protein or has a negative effect on expression of the gene. In a specific preferred embodiment the mutation results in the replacement of the codon coding for glutamic acid with a stop codon in position 209 of SEQ ID NO. 6 of the $IIC^{Man}$ protein of the glucose/mannose phosphotransferase system (not shown). Preferably, the mutation results in the replacement of a G with a T in position 625 of SEQ ID NO. 5.

In a preferred embodiment of the invention the glucose-deficient *Streptococcus thermophilus* strain is selected from the group consisting of: DSM 32227; DSM 28889; DSM 25850; DSM 25851; DSM 26722 and mutant strains derived thereof obtained by using one of the deposited strains as mother strain, wherein said mutants have retained or further improved the glucose secreting property of its mother strain.

In the present context, the term "strains derived thereof" should be understood as strains derived, or strains which can be derived from a starter strain or mother strain by means of e.g. genetic engineering, radiation and/or chemical treatment.

The "strains derived thereof" can also be spontaneously occurring mutants. It is preferred that the "strains derived thereof" are functionally equivalent mutants, e.g. mutants that have substantially the same, or improved properties (e.g. regarding texture or fermentation of galactose) as their mother strain. Especially, the term "strains derived thereof" refers to strains obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a preferred embodiment less than 1%, less than 0.1%, less than 0.01%, less than 0.001% or even less than 0.0001% of the nucleotides in the bacterial genome of the mutant has been replaced with another nucleotide, deleted or inserted as compared to the mother strain.

In a further embodiment the glucose-deficient *Streptococcus thermophilus* strain of the invention is lactose-fermenting. Thus an advantage of the present invention is that the glucose-negative *Streptococcus thermophilus* strain will convert part of the lactose of the milk substrate to glucose to provide the fermented milk product with a natural sweetness hence reducing the need for adding sugar to the product and to lower the lactose content of the milk base for the benefit of consumers intolerant to lactose.

Method of Obtaining a Glucose-Deficient *Streptococcus thermophilus* Strain

The method of obtaining a glucose-deficient *Streptococcus thermophilus* strain comprise a step of providing a galactose-fermenting strain, i.e. a strain that is capable of using galactose as a carbohydrate source.

Galactose-fermenting strains may be obtained by a method comprising the step of streaking the bacteria to be tested on agar plates, such as M17 agar plates comprising a specified concentration of galactose as sole carbohydrate source such as e.g. 2% and identifying colonies able to grow on these plates.

The galactose-fermenting *Streptococcus thermophilus* strains are capable of growth in M17 medium+2% galactose and are defined herein by that they have the ability to lower the pH in M17 broth containing 2% galactose as sole carbohydrate to 5.5 or lower when inoculated from an overnight culture at 1% and incubated for 24 hours at 37° C.

Such galactose-positive strains have been described in WO2011/026863 (Chr. Hansen A/S) and WO2011/092300 (Chr. Hansen A/S).

Galactose-fermenting strains which are resistant to 2-deoxyglucose can be identified by correlating the growth pattern of the strain in M17 medium+2% galactose with the growth pattern in M17 medium+2% glucose.

A method for screening and isolating a glucose-deficient strain of *Streptococcus thermophilus* comprises the following steps:

a) providing a galactose-fermenting *Streptococcus thermophilus* mother strain;

b) selecting and isolating from a pool of mutant *Streptococcus thermophilus* strains derived from the mother strain a pool of mutant *Streptococcus thermophilus* strains which are resistant to 2-deoxyglucose; and c) selecting and isolating from the pool of mutant *Streptococcus thermophilus* strains which are resistant to 2-deoxyglucose a mutant *Streptococcus thermophilus* strain if the growth rate of the mutant *Streptococcus thermophilus* strain is higher in M17 medium+2% galactose than in M17 medium+2% glucose.

In one embodiment the method further comprises the step a1) subjecting the mother strain to mutagenization, such as subjecting the mother strain to a chemical and/or a physical mutagen.

In another embodiment the method further comprises a step d) selecting and isolating from a pool of 2-deoxyglucose resistant *Streptococcus thermophilus* strains obtained in step c) a *Streptococcus thermophilus* strain if the growth rate of the *Streptococcus thermophilus* strain is high in M17 medium+2% sucrose and reduced as compared to the growth rate of the mother strain in M17 medium+2% glucose. Preferably the growth rate of the *Streptococcus thermophilus* strain is zero or at least reduced to below 5%, below 10%, below 15%, below 20%, below 25%, below 30%, below 35%, below 40%, below 45%, below 50% as compared with the growth rate of the mother strain.

The glucose-deficiency of the *Streptococcus thermophilus* strain may be due to a change in the nucleotide sequence in the glcK gene which encodes the glucokinase protein. The change may be a mutation, an insertion and/or a deletion.

In one embodiment of the invention the glucose deficient *Streptococcus thermophilus* strain comprises a mutation, an insertion, and/or a deletion in the nucleotide sequence of the glcK gene.

Glucose-Fermenting Strains of the Composition of the Invention

The glucose-fermenting *Streptococcus thermophilus* strain of the composition of the invention may be any conventional *Streptococcus thermophilus* strain suitable for producing a fermented milk product.

In one embodiment of the invention the glucose-fermenting *Streptococcus thermophilus* strain is a lactose-fermenting *Streptococcus thermophilus* strain or a lactose-deficient *Streptococcus thermophilus* strain.

In one embodiment of the invention the glucose-fermenting *Streptococcus thermophilus* strain is the strain deposited with DSMZ under accession no. DSM 19242 or a glucose-fermenting mutant strain derived thereof.

The glucose-fermenting *Lactobacillus delbrueckii* ssp. *bulgaricus* strain of the composition of the invention may be any conventional *Lactobacillus delbrueckii* ssp. *bulgaricus* strain suitable for producing a fermented milk product.

In one embodiment of the invention the glucose-fermenting *Lactobacillus delbrueckii* ssp. *bulgaricus* strain is a lactose-deficient *Lactobacillus delbrueckii* ssp. *bulgaricus* strain.

In one embodiment of the invention the glucose-fermenting *Lactobacillus delbrueckii* ssp. *bulgaricus* strain is selected from the group of strains deposited with DSMZ under accession no. DSM 28910; DSM 22586; and glucose-fermenting mutant strains derived thereof.

The terms "deficient in lactose metabolism", "lactose-deficient" are used in the context of the present invention to characterize LAB which either partially or completely lost the ability to use lactose as a source for cell growth or maintaining cell viability. Respective LAB are capable of metabolizing one or more non-lactose carbohydrates selected from sucrose, galactose, glucose, fructose and/or another fermentable carbohydrate. Since these carbohydrates are not naturally present in milk in sufficient amounts to support fermentation by lactose-deficient mutants, it is necessary to add these carbohydrates to the milk. Lactose-deficient and partially lactose-deficient LAB can be characterized as white colonies on a medium containing lactose and X-Gal.

In connection with the present invention the term "X-Gal" means 5-bromo chloro-3-indolyl-beta-D-galacto-pyranoside, which is a chromogenic substrate for beta-galactosidase, which hydrolyses X-Gal into colorless galactose and 5-bromo-4-chloro-indoxyl, which spontaneously dimerizes to form a blue pigment.

In a particular embodiment of the invention, the lactose-deficient strain is a *Streptococcus thermophilus* strain and/or a *Lactobacillus delbrueckii* subsp. *bulgaricus* strain capable of metabolizing a non-lactose carbohydrate selected from the group consisting of sucrose, galactose, glucose and fructose, preferably sucrose. In a particular embodiment of the invention, the lactose-deficient strain is a *Streptococcus thermophilus* strain and/or a *Lactobacillus delbrueckii* ssp. *bulgaricus* strain capable of metabolizing galactose.

In a particular embodiment of the composition of the invention, the *Lactobacillus delbrueckii* ssp. *bulgaricus* strain is selected from the group consisting of the strain deposited with DSMZ under accession no. DSM 28910; and mutant strains derived thereof further characterized as having the ability to generate white colonies on a medium containing lactose and X-Gal.

Lactose-deficient strains may be obtained from a suitable lactose-fermenting mother strain by mutation. The lactose-deficient strains were selected after UV-mutagenesis as white colonies (indicating a lactose deficient phenotype) on a suitable medium, e.g. MRS agar plates with 1% lactose and 200 mg/ml X-Gal. Lactose-fermenting strains possesses β-galactosidase activity, and colonies of lacrosse-positive strain appear blue due to the activity of the β-galactosidase. As lactose-fermenting mother strain for producing a lactose-deficient strain, the *Lactobacillus delbrueckii* ssp. *bulgaricus* strain deposited with DSMZ under the accession No. DSM 19252 may be used.

Composition

The present invention relates to a composition for producing a fermented milk product comprising:

(i) a starter culture comprising a glucose-fermenting *Streptococcus thermophilus* (St) strain and a glucose-fermenting *Lactobacillus delbrueckii* subsp. *bulgaricus* (Lb) strain; and (ii) a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene.

In one embodiment the invention provides for a composition for producing a fermented milk product, wherein post-acidification of the fermented milk product is reduced as compared to a fermented milk product prepared by a composition without the glucose-deficient *Streptococcus thermophilus* (St) strain of (ii).

In one embodiment the post-acidification of the fermented milk product is reduced with more than 5%, more than 10%, more than 15%, more than 20%, more than 25%, more than 30%, more than 35%, more than 40%, more than 45%, or more than 50% as compared to a fermented milk product prepared by a composition without the glucose-deficient *Streptococcus thermophilus* (St) strain of (ii).

The composition of the invention comprises from $10^4$ to $10^{12}$ CFU (colony forming units)/g of the glucose-deficient *Streptococcus thermophilus* strain, such as from $10^5$ to $10^{11}$ CFU/g, such as from $10^6$ to $10^{10}$ CFU/g, or such as from $10^7$ to $10^9$ CFU/g of the glucose-deficient *Streptococcus thermophilus* strain.

In one embodiment of the invention the glucose-deficient *Streptococcus thermophilus* strain is lactose-fermenting.

In one embodiment, the glucose-deficient *Streptococcus thermophilus* strain of the composition is unable to acidify a 9.5% B-milk, defined as resulting in a pH decrease of less than 1.0 when a 9.5% B-milk is inoculated with $10^6$-$10^7$ CFU/ml of the glucose-deficient *Streptococcus thermophilus* strain and incubated for 14 hours at 40° C., and the composition further comprises an amount of a compound, which can trigger acidification of the a 9.5% B-milk by the glucose-deficient *Streptococcus thermophilus* strain DSM 32227; DSM 28889; DSM 25850; DSM 25851; or DSM 26722, defined as resulting in a pH decrease of 1.0 or more when a 9.5% B-milk is inoculated with $10^6$-$10^7$ CFU/ml of the glucose-deficient *Streptococcus thermophilus* strain and incubated for 14 hours at 40° C. In an embodiment, the compound is sucrose. Preferably, the amount of sucrose is from 0.000001% to 2%, such as from 0.00001% to 0.2%, such as from 0.0001% to 0.1%, such as from 0.001% to 0.05%.

In one embodiment, the composition further comprises from $10^4$ to $10^{12}$ CFU/g of a conventional *Lactobacillus delbrueckii* subsp. *bulgaricus* strain, such as from $10^5$ to $10^{11}$ CFU/g, such as from $10^6$ to $10^{10}$ CFU/g, or such as from $10^7$ to $10^9$ CFU/g of the *Lactobacillus delbrueckii* subsp. *bulgaricus* strain.

In one embodiment, the composition comprises at least two *Streptococcus thermophilus* (St) strains, at least three St strains, or at least four St strains. In a further embodiment, the composition comprises two, St strains, three St strains, or four St strains. In a particular embodiment of the invention, the composition comprises no more than three *Lactobacillus delbrueckii* subsp. *bulgaricus* (Lb) strains, preferably no more than two Lb strains, or more preferably one Lb strain.

In a particular embodiment of the invention, the composition comprises at least one *Streptococcus thermophilus* strain selected from: DSM 32227; DSM 28889; DSM 25850; and DSM 26722, and the *Lactobacillus delbrueckii* subsp. *bulgaricus* strain DSM 28910.

*Lactobacillus delbrueckii* subsp. *bulgaricus, Streptococcus thermophilus* and other lactic acid bacteria are commonly used as starter cultures serving a technological purpose in the production of various foods. In the dairy industry such starter cultures are used in the production of fermented milk products such as e.g. yoghurt. Thus, in one embodiment of the invention the composition is a starter culture. In one embodiment of the invention the composition is used as a starter culture. In one embodiment of the invention the composition is used as a starter culture for production of yoghurt. In one embodiment of the invention the composition is used as a starter culture for production of yoghurt with reduced or low post-acidification. The level of post-acidification is defined in comparison with a yoghurt prepared with a similar composition or starter culture without the glucose-deficient *Streptococcus thermophilus* strain.

The composition of the present invention may be provided in several forms. It may be a frozen form, dried form, freeze dried form, or liquid form. Thus, in one embodiment the composition is in frozen, dried, freeze-dried or liquid form.

The composition of the present invention may additionally comprise cryoprotectants, lyoprotectants, antioxidants, nutrients, fillers, flavorants or mixtures thereof. The composition preferably comprises one or more of cryoprotectants, lyoprotectants, antioxidants and/or nutrients, more preferably cryoprotectants, lyoprotectants and/or antioxidants and most preferably cryoprotectants or lyoprotectants, or both. Use of protectants such as cryoprotectants and lyoprotectant are known to a skilled person in the art. Suitable cryoprotectants or lyoprotectants include mono-, di-, tri- and polysaccharides (such as glucose, mannose, xylose, lactose, sucrose, trehalose, raffinose, maltodextrin, starch and gum arabic (acacia) and the like), polyols (such as erythritol, glycerol, inositol, mannitol, sorbitol, threitol, xylitol and the like), amino acids (such as proline, glutamic acid), complex substances (such as skim milk, peptones, gelatin, yeast extract) and inorganic compounds (such as sodium tripolyphosphate). In one embodiment, the composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds. Suitable antioxidants include ascorbic acid, citric acid and salts thereof, gallates, cysteine, sorbitol, mannitol, maltose. Suitable nutrients include sugars, amino acids, fatty acids, minerals, trace elements, vitamins (such as vitamin B-family, vitamin C). The composition may optionally comprise further substances including fillers (such as lactose, maltodextrin) and/or flavorants.

Method of Producing a Fermented Milk Product

The invention is further directed to a method of producing a fermented milk product comprising inoculating and fermenting a milk substrate with the composition according to the present invention. The composition is described in detail in the section "Composition" above.

In one embodiment the invention relates to a method for producing a fermented milk product comprising inoculating and fermenting a milk base with (i) a starter culture comprising a glucose-fermenting *Streptococcus thermophilus* (St) strain and a glucose-fermenting *Lactobacillus delbrueckii* subsp. *bulgaricus* (Lb) strain; and (ii) a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene.

In one embodiment the invention relates to a method of producing a fermented milk product, wherein post-acidification of the fermented milk product is reduced as compared to a fermented milk product prepared by a composition without the glucose-deficient *Streptococcus thermophilus* (St) strain of (ii).

In one embodiment the invention relates to a method for producing a fermented milk product comprising inoculating and fermenting a milk base with (i) a starter culture comprising a glucose-fermenting *Streptococcus thermophilus* (St) strain and a glucose-fermenting *Lactobacillus delbrueckii* subsp. *bulgaricus* (Lb) strain; and (ii) a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene, wherein post-acidification of the fermented milk product is reduced as compared to a fermented milk product prepared without the glucose-deficient *Streptococcus thermophilus* (St) strain of (ii).

The term "milk" is to be understood as the lacteal secretion obtained by milking any mammal, such as a cow, a sheep, a goat, a buffalo or a camel. In a preferred embodiment, the milk is cow's milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate wholly or partly from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid. Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

The term "fermented milk product" as used herein refers to a food or feed product wherein the preparation of the food or feed product involves fermentation of a milk substrate with lactic acid bacteria. "Fermented milk product" as used herein includes but is not limited to products such as thermophilic fermented milk products, e.g. yoghurt, mesophilic fermented milk products, e.g. sour cream and buttermilk, as well as fermented whey.

The term "thermophile" herein refers to microorganisms that thrive best at temperatures above 35° C. The industrially most useful thermophilic bacteria include *Streptococcus* spp. and *Lactobacillus* spp. The term "thermophilic fermentation" herein refers to fermentation at a temperature above about 35° C., such as between about 35° C. to about 45° C. The term "thermophilic fermented milk product" refers to fermented milk products prepared by thermophilic fermentation of a thermophilic starter culture and include such fermented milk products as set-yoghurt, stirred-yoghurt and drinking yoghurt, e.g. Yakult.

The term "mesophile" herein refers to microorganisms that thrive best at moderate temperatures (15° C.-35° C.). The industrially most useful mesophilic bacteria include *Lactococcus* spp. and *Leuconostoc* spp. The term "mesophilic fermentation" herein refers to fermentation at a temperature between about 22° C. and about 35° C. The term "mesophilic fermented milk product" refers to fermented milk products prepared by mesophilic fermentation of a mesophilic starter culture and include such fermented milk products as buttermilk, sour milk, cultured milk, smetana, sour cream, Kefir and fresh cheese, such as quark, tvarog and cream cheese.

In a preferred embodiment the concentration of *Streptococcus thermophilus* cells inoculated is from $10^4$ to $10^9$ CFU *Streptococcus thermophilus* cells per ml of milk substrate, such as from $10^4$ CFU to $10^8$ CFU *Streptococcus thermophilus* cells per ml of milk substrate.

In another preferred embodiment of the method of the invention the *Streptococcus thermophilus* strain is unable to acidify a 9.5% B-milk, defined as resulting in a pH decrease of less than 1.0 when the 9.5% B-milk is inoculated with $10^6$-$10^7$ CFU/ml of the *Streptococcus thermophilus* strain and incubated for 14 hours at 40° C., and the milk substrate is added an amount of a compound, effective to trigger acidification of the 9.5% B-milk by the *Streptococcus thermophilus* strain, defined as resulting in a pH decrease of 1.0 or more when a 9.5% B-milk is inoculated with $10^6$-$10^7$ CFU/ml of the *Streptococcus thermophilus* strain and incubated for 14 hours at 40° C. Preferably, the compound is sucrose. Preferably, the amount of sucrose is from 0.000001% to 2%, such as from 0.00001% to 0.2%, such as from 0.0001% to 0.1%, such as from 0.001% to 0.05%.

In the present context, a yoghurt starter culture is a bacterial culture which comprises at least one *Lactobacillus delbrueckii* subsp. *bulgaricus* strain and at least one *Streptococcus thermophilus* strain. In accordance herewith, the term "yoghurt" refers to a fermented milk product obtainable by inoculating and fermenting milk with a composition comprising a *Lactobacillus delbrueckii* subsp. *bulgaricus* strain and a *Streptococcus thermophilus* strain.

In a further embodiment the invention relates to a method for reducing post-acidification in a fermented milk product prepared by a starter culture comprising a glucose-fermenting *Streptococcus thermophilus* (St) strain and a glucose-fermenting *Lactobacillus delbrueckii* subsp. *bulgaricus* (Lb) strain by adding to a milk base a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene, In one embodiment the glucose-deficient St strain may be lactose-fermenting.

In any embodiment of the invention the starter culture and the glucose-deficient *Streptococcus thermophilus* (St) strain may be added as a mixture or as a kit-of-part.

Fermented Milk Product

The present invention further relates to a fermented milk product comprising the composition according to the invention. In a preferred embodiment the fermented milk product may be a yoghurt, a cheese, sour cream and buttermilk as well as fermented whey. Preferably, the fermented milk product is a yoghurt.

In one embodiment the invention relates to a fermented milk product, wherein post-acidification of the fermented milk product is reduced as compared to a fermented milk product prepared by a composition without the glucose-deficient *Streptococcus thermophilus* (St) strain of (ii).

In one embodiment the fermented milk product is made by the method for producing a fermented milk product comprising inoculating and fermenting a milk substrate with the composition according to the invention. In one embodiment the composition of the invention comprises one or more glucose-deficient *Streptococcus thermophilus* strains, one or more glucose-fermenting *Streptococcus thermophilus* strains and one or more glucose-fermenting *Lactobacillus delbrueckii* subsp. *bulgaricus* strains.

In one embodiment the one or more glucose-deficient *Streptococcus thermophilus* strain of the composition is selected from the group consisting of: DSM 32227; DSM 28889; DSM 25850; DSM 25851; DSM 26722; and glucose-deficient mutant strains derived thereof.

In one embodiment the one or more glucose-fermenting *Streptococcus thermophilus* strain of the composition is selected from the group consisting of: DSM 19242; DSM 22935; and glucose-fermenting mutant strains derived thereof.

In one embodiment the one or more glucose-fermenting *Lactobacillus delbrueckii* subsp. *bulgaricus* strains of the composition is selected from the group consisting of: DSM 28910; DSM 22586; and glucose-fermenting mutant strains derived thereof.

In one embodiment the fermented milk product comprises one or more of the strains selected from DSM 28889, and one or more of the strains selected from DSM 19242 and DSM 22586.

In one embodiment the fermented milk product comprises the strain DSM 28889, DSM 19242, and DSM 22586.

In one embodiment the fermented milk product comprises the strain DSM 28889 and DSM 22935.

Use of the Composition of the Invention

The invention relates to a use of the composition according to the invention for the preparation of a fermented milk product.

In one embodiment the invention relates to the use of the composition of the invention, wherein post-acidification of the fermented milk product is reduced as compared to a fermented milk product prepared by a composition without the glucose-deficient *Streptococcus thermophilus* (St) strain.

In one embodiment the invention related to the use of (i) a starter culture comprising a glucose-fermenting *Streptococcus thermophilus* (St) strain and a glucose-fermenting *Lactobacillus delbrueckii* subsp. *bulgaricus* (Lb) strain; and (ii) a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene, for reducing post-acidification of a fermented milk product as compared to a fermented milk product prepared without the glucose-deficient *Streptococcus thermophilus* (St) strain of (ii).

In one embodiment the invention relates to the use of a glucose-deficient *Streptococcus thermophilus* (St) strain, wherein said St strain is galactose-fermenting and carries a mutation in the DNA sequence of the glcK gene encoding a glucokinase protein, which mutation inactivates the glucokinase protein or has a negative effect on expression of the gene, for reducing post-acidification of a fermented milk product as compared to a fermented milk product prepared without the glucose-deficient *Streptococcus thermophilus* (St) strain. The glucose-deficient St strain may be lactose-fermenting.

Embodiments of the present invention are described below, by way of non-limiting examples.

SEQUENCE LISTING

SEQ ID NO. 1 shows the DNA sequence of the mutated glucokinase gene of strain DSM 28889.

SEQ ID NO. 2 shows the amino acid sequence encoded by SEQ ID NO. 1.

SEQ ID NO. 3 shows the DNA sequence of the mutated ManN gene of strain DSM 28889.

SEQ ID NO. 4 shows the amino acid sequence encoded by SEQ ID NO. 3.

SEQ ID NO. 5 shows the DNA sequence of the ManM gene (not mutated) of strain DSM 28889.

SEQ ID NO. 6 shows the amino acid sequence encoded by SEQ ID NO. 5.

EXAMPLES

Materials and Methods

Medium:

For *Streptococcus thermophilus*, the medium used is the M17 medium known to persons skilled in the art.

TABLE 1

| The M17 agar medium has the following composition per liter $H_2O$ with a final pH $7.1 \pm 0.2$ ($25°$ C.): | |
| --- | --- |
| agar, | 12.75 g |
| ascorbic acid | 0.5 g |
| casein peptone (tryptic) | 2.5 g |
| disodium β-glycerophosphate pentahydrate | 19 g |
| magnesium sulfate hydrate | 0.25 g |
| meat extract | 5 g |
| meat peptone (peptic) | 2.5 g |
| soya peptone (papainic) | 5 g |
| yeast extract | 2.5 g |

TABLE 2

| M17 broth has the following composition per liter H₂O and final pH 7.0 ± 0.2 (25° C.) | |
| --- | --- |
| ascorbic acid | 0.5 g |
| magnesium sulfate | 0.25 g |
| meat extract | 5 g |
| meat peptone (peptic) | 2.5 g |
| sodium glycerophosphate | 19 g |
| soya peptone (papainic) | 5 g |
| tryptone | 2.5 g |
| yeast extract | 2.5 g |

Carbon sources added are sterile lactose 20 g/I, glucose 20 g/I or galactose 20 g/I.

As known to the skilled person, the M17 medium is a medium that is considered to be suitable for growth of *Streptococcus thermophilus*. Further, as understood by the skilled person, in the present context, a M17 concentrate may be supplied from different suppliers and independently of the specific supplier one will (within standard measurement uncertainty) get the same herein relevant result of 2-deoxyglucose resistance for a herein relevant cell of interest.

The medium used for culturing *Lactobacillus delbrueckii* subsp. *bulgaricus* was MRS-IM medium. MRS-IM was used either in the form of agar plates or broth.

TABLE 3

| The MRS-IM agar medium had the following composition per liter H₂O. The pH was adjusted after autoclaving to 6.9 ± 0.1 at 25° C. | | |
| --- | --- | --- |
| Tryptone | Oxoid L 42 | 10.0 g |
| Yeast extract | Oxoid L 21 | 5.0 g |
| Tween 80 | Merck nr 8.22187 | 1.0 g |
| K₂HPO₄ | Merck nr 105104 | 2.6 g |
| Na-acetate | Merck nr 106267 | 5.0 g |
| Diammonium-hydrogen-citrate | Merck nr 101154 | 2.0 g |
| MgSO₄, 7 H2O | Merck nr 105882 | 0.2 g |
| MnSO₄, H2O | Merck nr 105941 | 0.05 g |
| Agar | SO-BI-GEL | 13.0 g |

TABLE 4

| The MRS-IM broth used in the below examples for liquid cultures had the following composition per liter H₂O. The pH is adjusted after autoclaving to 6.9 ± 0.1 at 25° C. The carbon sources, lactose 20 g/l or glucose 20 g/l, were first filtered sterile and then added to the autoclaved broth. | | |
| --- | --- | --- |
| Tryptone | Oxoid L 42 | 10.0 g |
| Yeast extract | Oxoid L 21 | 5.0 g |
| Tween 80 | Merck nr 8.22187 | 1.0 g |
| K₂HPO₄ | Merck nr 105104 | 2.6 g |
| Na-acetate | Merck nr 106267 | 5.0 g |
| Diammonium-hydrogen-citrate | Merck nr 101154 | 2.0 g |
| MgSO₄, 7 H2O | Merck nr 105882 | 0.2 g |
| MnSO₄, H2O | Merck nr 105941 | 0.05 g |
| Agar | SO-BI-GEL | 13.0 g |

The above MRS-IM media can be varied to some extent without affecting the capability of the media to support growth of *Lactobacillus delbrueckii* subsp. *bulgaricus*. Further, as will be understood by the skilled person, a MRS-IM concentrate or the various components described above may be obtained from different suppliers and used for the preparation of a MRS-IM medium. These media will likewise be used in the below examples, in particular in the 2-deoxyglucose resistance selection assay.

Example 1: Post-Acidification for a Commercial Yoghurt Culture without and with Addition of Glucose-Deficient *Streptococcus thermophilus* Strain DSM 28889

Cultures

Culture 1: Premium 4

Culture 2: Premium 4+DSM 28889

DSM 28889 is a glucose-deficient, galactose-fermenting and lactose-fermenting *Streptococcus thermophilus* strain.

Premium 4 is a commercial yoghurt starter culture sold by Chr. Hansen A/S comprising two glucose-fermenting *Streptococcus thermophilus* strains and one glucose-fermenting *Lactobacillus delbrueckii* subsp. *bulgaricus* strain. All three strains are lactose-fermenting

TABLE 5

| Yoghurt production process parameters | |
| --- | --- |
| Milk Base | 4% protein; 3% fat; 5% sucrose |
| Heat treatment of milk base | 95° C./5 min. (Pasteurizer) |
| Fermentation temperature | 38° C. |
| Target pH | 4.60 |
| Inoculation rate: Standard culture | 0.02% |
| Inoculation rate: Standard culture + lactose-deficient strain | 0.01% + 0.04% |
| Type of yoghurt | Set yoghurt |

A yoghurt starter culture was tested with and without addition of the glucose-deficient strain DSM 28889 (5 times 2 samples) for yoghurt production at a laboratory scale. The milk base was heated to 38° C., then inoculated with the cultures previously thawn and diluted in milk prior to addition to 3 L vats. The inoculated milk base was poured into 100 g yoghurt cups (duplicate) and maintained at 38° C. in an incubator, then moved to a cooling room when pH 4.6 was reached (set yoghurt process). At Day 1, a set of yoghurt cups with the samples tested were placed in a 13° C. incubator and stored until 29 days, while an identical set of cups was kept at 5° C. in a cold room until 29 days.

Results

Acidification

Culture 1 was 468 minutes to reach a pH of 4.6. Culture 2 was 752 minutes to reach a pH of 4.6.

Post-Acidification

TABLE 6

| Post-acidification (pH) | | | | | |
| --- | --- | --- | --- | --- | --- |
| | Day 0 | Day 9 | Day 15 | Day 23 | Day 29 |
| Culture 1 (5° C.) | 4.64 | 4.46 | 4.45 | 4.45 | 4.40 |
| Culture 1 (13° C.) | 4.64 | 4.32 | 4.25 | 4.24 | na |
| Culture 2 (5° C.) | 4.69 | 4.63 | 4.64 | 4.65 | 4.62 |
| Culture 2 (13° C.) | 4.69 | 4.65 | 4.59 | 4.60 | 4.58 |

The post-acidification was reduced at both the tested temperatures in the presence of DSM 28889.

Carbohydrates

TABLE 7

Carbohydrate profile of yoghurt after storage for 21 days at 5° C. (mg/g)

|  | Sucrose | Lactose | Glucose | Galactose | Fructose |
|---|---|---|---|---|---|
| Culture 1 (5° C.) | 41.9 | 40.8 | 1.6 | 5.7 | 0.0 |
| Culture 2 (5° C.) | 38.4 | 26.8 | 9.7 | 8.5 | 1.0 |

Deposits and Expert Solutions

The applicant requests that a sample of the deposited microorganisms stated below may only be made available to an expert, until the date on which the patent is granted.

TABLE 8

Deposits were made according to the Budapest treaty on the international recognition of the deposit of microorganisms for the purposes of patent procedure at Deutsche Sammlung von Mikroorganismen und Zellkulturen (DSMZ) GmbH, In-hoffenstr. 7B, D-38124 Braunschweig, Germany.

| Strain | Accession No. | Deposit date |
|---|---|---|
| Streptococcus thermophilus | DSM 19242 | Mar. 29, 2007 |
| Streptococcus thermophilus | DSM 22934 | Sep. 08, 2009 |
| Streptococcus thermophilus | DSM 22935 | Sep. 09, 2009 |
| Streptococcus thermophilus | DSM 25838 | Apr. 03, 2012 |
| Streptococcus thermophilus | DSM 25850 | Apr. 03, 2012 |
| Streptococcus thermophilus | DSM 25851 | Apr. 03, 2012 |
| Streptococcus thermophilus | DSM 26722 | Dec. 12, 2012 |
| Streptococcus thermophilus | DSM 28889 | Jun. 04, 2014 |
| Streptococcus thermophilus | DSM 32227 | Dec. 08, 2015 |
| Lactobacillus delbrueckii subsp. bulgaricus | DSM 19252 | Apr. 03, 2007 |
| Lactobacillus delbrueckii subsp. bulgaricus | DSM 22586 | May 19, 2009 |
| Lactobacillus delbrueckii subsp. bulgaricus | DSM 28910 | Jun. 12, 2014 |

STATEMENT REGARDING BIOLOGICAL DEPOSITS

The strain of Streptococcus thermophilus referred to herein as DSM 32227 was deposited under the provisions of the Budapest Treaty at Deutsche Sammlung von Mikroorganismen und Zellkulturen GmbH (the German Collection of Microorganisms and Cell Cultures or DSMZ) (Braunschweig, Germany) under accession number DSM 32227 on Dec. 8, 2015.

The strain of Streptococcus thermophilus referred to herein as DSM 28889 was deposited under the provisions of the Budapest Treaty at Deutsche Sammlung von Mikroorganismen und Zellkulturen GmbH (the German Collection of Microorganisms and Cell Cultures or DSMZ) (Braunschweig, Germany) under accession number DSM 28889 on Jun. 4, 2014.

The strain of Streptococcus thermophilus referred to herein as DSM 25850 was deposited under the provisions of the Budapest Treaty at Deutsche Sammlung von Mikroorganismen und Zellkulturen GmbH (the German Collection of Microorganisms and Cell Cultures or DSMZ) (Braunschweig, Germany) under accession number DSM 25850 on Apr. 3, 2012.

The strain of Streptococcus thermophilus referred to herein as DSM 25851 was deposited under the provisions of the Budapest Treaty at Deutsche Sammlung von Mikroorganismen und Zellkulturen GmbH (the German Collection of Microorganisms and Cell Cultures or DSMZ) (Braunschweig, Germany) under accession number DSM 25851 on Apr. 3, 2012.

The strain of Streptococcus thermophilus referred to herein as DSM 26722 was deposited under the provisions of the Budapest Treaty at Deutsche Sammlung von Mikroorganismen und Zellkulturen GmbH (the German Collection of Microorganisms and Cell Cultures or DSMZ) (Braunschweig, Germany) under accession number DSM 26722 on Dec. 12, 2012.

The bacterial strains described above have been deposited under conditions that access to the material will be available during the pendency of the present patent application to one determined by the Commissioner to be entitled thereto under 37 C.F.R. 1.14 and 35 U.S.C. § 122. All restrictions on the availability to the public of the deposited materials will be irrevocably removed upon the granting of a patent from the above-identified application. The deposited materials will be maintained with all the care necessary to keep the materials viable and uncontaminated for a period of at least five years after the most recent request for the furnishing of a sample of the deposited microorganism, and in any case, for a period of at least thirty (30) years after the date of deposit for the enforceable life of the patent, whichever period is longer.

REFERENCES

WO2006/042862
US2010/0021586
WO2010/139765
WO2011/026863
WO2011/092300
WO2013/160413
WO2013/169205
WO2015/193459
WO2017/167660
Porter et al. (1982) Biochim. Biophys. Acta, 709:178-186
Godshall (1988) Food Technology 42(11):71-78
Cochu et al. (2003) Appl and Environ Microbiol, 69(9): 5423-5432
Pool et al. (2006) Metabolic Engineering 8(5):456-464

The invention claimed is:

1. A composition for producing a fermented milk product with reduced post-acidification, comprising:

(i) a conventional starter culture comprising a lactose-fermenting and glucose-fermenting *Streptococcus thermophilus* (St) strain and a lactose-fermenting, glucose-fermenting *Lactobacillus delbrueckii* subsp. *bulgaricus* (Lb) strain; and (ii) a lactose-fermenting, glucose-deficient *Streptococcus thermophilus* (St) strain, wherein said glucose-deficient St strain is galactose-fermenting and carries a mutation in a glck gene DNA sequence encoding a glucokinase protein, wherein the mutation inactivates the glucokinase protein or has a negative effect on expression of the gene;

wherein the fermented milk product has reduced post-acidification compared to a fermented milk product prepared with a composition that does not comprise the glucose-deficient *Streptococcus thermophilus* (St) strain.

2. The composition according to claim 1, wherein the glucose-deficient St strain is 2-deoxyglucose resistant.

3. The composition according to claim 1, wherein the glucose-deficient St strain carries a mutation that reduces transport of glucose into a cell of the strain.

4. The composition according to claim 1, wherein the glucose-deficient St strain increases an amount of glucose in a 9.5% B-milk to at least 5 mg/ml when inoculated in the 9.5% B-milk at a concentration of $10^6$-$10^7$ CFU/ml and grown at 40° C. for 20 hours.

5. The composition according to claim 1, wherein the glucose-deficient St strain increases an amount of glucose in a 9.5% B-milk comprising 0.05% sucrose to at least 5 mg/ml when inoculated in the 9.5% B-milk comprising 0.05% sucrose at a concentration of $10^6$-$10^7$ CFU/ml and grown at 40° C. for 20 hours.

6. The composition according to claim 1, wherein the glucose-deficient St strain is selected from the group consisting of St strains deposited at Deutsche Sammlung von Mikroorganismen und Zellkulturen (Braunschweig, Germany) (DSMZ) under accession numbers DSM 32227; DSM 28889; DSM 25850; DSM 25851; and DSM 26722; and mutant strains derived therefrom which mutant strains are obtained by using one of the deposited strains as a mother strain, and wherein said mutant strains exhibit a glucose secreting activity that is retained or greater than that of the respective mother strain.

7. A method for producing a fermented milk product with reduced post-acidification, comprising inoculating and fermenting a milk substrate with the composition according to claim 1, wherein the fermented milk product has reduced post-acidification compared to a fermented milk product prepared with a composition that does not comprise the glucose-deficient *Streptococcus thermophilus* (St) strain.

8. A fermented milk product obtained by the method of claim 7.

9. The composition according to claim 1, wherein the glucose-deficient St strain is deposited at Deutsche Sammlung von Mikroorganismen und Zellkulturen (Braunschweig, Germany) (DSMZ) under accession number DSM 32227, and mutant strains derived therefrom wherein the mutant strains are obtained by using strain DSM 32227 as a mother strain, and wherein said mutant strains exhibit a glucose secreting activity that is retained or greater than that of the respective mother strain.

10. The composition according to claim 1, wherein the glucose-deficient St strain is deposited at Deutsche Sammlung von Mikroorganismen und Zellkulturen (Braunschweig, Germany) (DSMZ) under accession number DSM 28889, and mutant strains derived therefrom wherein the mutant strains are obtained by using strain DSM 28889 as a mother strain, and wherein said mutant strains exhibit a glucose secreting activity that is retained or greater than that of the respective mother strain.

11. The composition according to claim 1, wherein the glucose-deficient St strain is deposited at Deutsche Sammlung von Mikroorganismen und Zellkulturen (Braunschweig, Germany) (DSMZ) under accession number DSM 25850, and mutant strains derived therefrom wherein the mutant strains are obtained by using strain DSM 25850 as a mother strain, and wherein said mutant strains exhibit a glucose secreting activity that is retained or greater than that of the respective mother strain.

12. The composition according to claim 1, wherein the glucose-deficient St strain is deposited at Deutsche Sammlung von Mikroorganismen und Zellkulturen (Braunschweig, Germany) (DSMZ) under accession number DSM 25851, and mutant strains derived therefrom wherein the mutant strains are obtained by using strain DSM 25851 as a mother strain, and wherein said mutant strains exhibit a glucose secreting activity that is retained or greater than that of the respective mother strain.

13. The composition according to claim 1, wherein the glucose-deficient St strain is deposited at Deutsche Sammlung von Mikroorganismen und Zellkulturen (Braunschweig, Germany) (DSMZ) under accession number DSM 26722, and mutant strains derived therefrom wherein the mutant strains are obtained by using strain DSM 26722 as a mother strain, and wherein said mutant strains exhibit a glucose secreting activity that is retained or greater than that of the respective mother strain.

* * * * *